United States Patent
Suzuki et al.

(10) Patent No.: US 7,722,934 B2
(45) Date of Patent: May 25, 2010

(54) BIOLOGICAL REPAIR MATERIAL COMPATIBLE WITH BIOLOGICAL TISSUE ADHESIVE

(75) Inventors: Yoshiaki Suzuki, Tokyo (JP); Hiroshi Ujiie, Tokyo (JP); Noriyoshi Takahashi, Saitama (JP); Masaya Iwaki, Saitama (JP)

(73) Assignee: Riken, Saitama (JP)

( * ) Notice: Subject to any disclaimer, the term of this patent is extended or adjusted under 35 U.S.C. 154(b) by 496 days.

(21) Appl. No.: 10/525,724

(22) PCT Filed: Aug. 29, 2003

(86) PCT No.: PCT/JP03/11048

§ 371 (c)(1), (2), (4) Date: Dec. 6, 2005

(87) PCT Pub. No.: WO2004/026355

PCT Pub. Date: Apr. 1, 2004

(65) Prior Publication Data

US 2006/0155041 A1 Jul. 13, 2006

(30) Foreign Application Priority Data

Aug. 30, 2002 (JP) .............................. 2002-253322

(51) Int. Cl.
B05D 3/06 (2006.01)

(52) U.S. Cl. .................. 427/496; 427/533; 427/536

(58) Field of Classification Search ................. 204/164, 204/165, 169; 428/411.1, 422, 480, 543
See application file for complete search history.

(56) References Cited

U.S. PATENT DOCUMENTS

| | | | |
|---|---|---|---|
| 5,152,783 A | 10/1992 | Suzuki et al. | |
| 5,308,704 A | 5/1994 | Suzuki et al. | |
| 5,891,192 A * | 4/1999 | Murayama et al. | 623/1.48 |
| 5,906,824 A | 5/1999 | Suzuki et al. | |
| 6,051,751 A | 4/2000 | Sioshansi et al. | |
| 6,503,527 B1 * | 1/2003 | Whitmore et al. | 424/422 |
| 6,872,759 B2 | 3/2005 | Suzuki et al. | |
| 2002/0155295 A1 * | 10/2002 | Suzuki et al. | 428/409 |
| 2004/0005364 A1 * | 1/2004 | Klein et al. | 424/618 |

FOREIGN PATENT DOCUMENTS

| | | |
|---|---|---|
| EP | 1252902 | 10/2002 |
| JP | 112560 | 5/1991 |
| JP | 049689 | 2/1993 |
| JP | 5-208042 | 8/1993 |
| JP | 7-500 | 1/1995 |
| JP | 2000-129015 | 5/2000 |

OTHER PUBLICATIONS

English language translation of Suzuki et al., Ionics, vol. 25, No. 1, pp. 47-54, 1999.*
Yoshiaki Suzuki et al., "Ion Beam Irradiated Expanded Polytetrafluoroethylene for the Development of Dura Mater", Ionics, vol. 27, No. 7, pp. 3-11 (2001).
Yoshiaki Suzuki et al., "Biomedical Application of Ion Beam Irradiated Polymeric Materials", Ionics, vol. 25, No. 6, pp. 47-54 (1999).
Masayoshi Izukawa et al., "Nerve Cell Attachment Property of Absorbable Poly-Lactic-Acid Modified by Carbon Negative-Ion Implantation", J. Vac. Soc. Jpn., vol. 45, No. 6, pp. 514-518 (2002).
English language Abstract of JP 2000-129015.
English language Abstract of JP 7-500.
Yoshiteru Suzuki et al., "Ion Beam Ni Yoru ePTFE Jinko Komaku No Kaishitsu—Soshiki Oyobi Fibrin Nori Saibo Secchakusei No Fuyo-", The Society of Polymer Science, Japan Yokoshu, vol. 52, No. 5, pp. 1152 (2003).
Noriyoshi Takahashi et al., "Ion Beam Shosha Ni Yoru ePTFE Jinko Komaku No Kairyo", Three Beams Gijutsu Ni yoru Hyomen Kaishitsu to Kaiseki Yokoshu Riken Symposium, Heisei 15 Nen, pp. 24 (2003).
English Language Abstract of JP 3-112560, published May 14, 1991.
English Language Abstract of JP 5-049689, published Feb. 3, 1993.
Kobayashi et al., "Surface Modification of silicone sheets and tubes using plasma-based ion implantation" Surface & Coatings Technology 201 (2007) 8039-8042.

* cited by examiner

*Primary Examiner*—Ramsey Zacharia
(74) *Attorney, Agent, or Firm*—Greenblum & Bernstein, P.L.C.

(57) ABSTRACT

An object of the present invention is to provide a means for improving the affinity of an in vivo embedded material such as an artificial blood vessel or an artificial dura mater with a tissue adhesive, so as to quickly prevent the leakage of the blood or spinal fluid. The present invention provides a polymeric material used in combination with a tissue adhesive, which comprises carbon or silicon as a constitutional element, and at least a portion of the surface of which is modified by ion bombardment.

15 Claims, 3 Drawing Sheets

A, D: acrylic made
B, C: ePTFE sheet a = 17mm
b = 15mm
c = 10mm
d = 18mm
e = 34mm

BIOLOGICAL REPAIR MATERIAL COMPATIBLE WITH BIOLOGICAL TISSUE ADHESIVE

TECHNICAL FIELD

The present invention relates to a repair material having an affinity with a tissue adhesive, that is, a polymeric material that is used in combination with a tissue adhesive. More specifically, the present invention relates to a polymeric material that is used in combination with a tissue adhesive, at least a portion of the surface of which is modified by ion bombardment, thereby resulting in an improved affinity with the tissue adhesive, and a production method thereof.

BACKGROUND ART

Among three-layer membranes (pia mater, cranial arachnoid mater, and cranial dura mater) that are present in the cranial bone and protect the brain parenchyma, the cranial dura mater is hardest and exists as the outermost layer of the three aforementioned layers. Thus, the cranial dura mater is also considered to be the inner periosteum of the cranial bone. When neurosurgical operations are conducted, the cranial dura mater must be excised in many cases, thereby resulting in the absence of the cranial dura mater. In addition, there may also be cases where spontaneous contraction of the cranial dura mater per se makes the primary suture difficult. If the operative site were sutured without closing the cranial dura mater, it would cause serious complications. For example, it could cause a leakage of spinal fluid, which may result in development of an intracranial infection, or it could cause the adhesion of the brain parenchyma to the bone or subcutaneous tissues, which may lead to local nervous symptoms or become a focal point of a seizure. Thus, when the operative site is sutured, a strict suture is required, so as to avoid the formation of gaps on the cranial dura mater. Accordingly, in a case where a part of the cranial dura mater is lost, or where the primary suture becomes difficult, it is necessary to completely suture the operative site using a certain supply material, so as to prevent the formation of gaps.

The type of a supply material that is used to compensate for the absence of the cranial dura mater has been an important issue for a long period of time, and has been discussed by neurosurgeons. Artificial materials were initially used for a while, but they have been problematic in terms of biocompatibility, handlability, etc. Thus, such artificial materials were soon abandoned. Auto fascia has most widely been used from the initial stage to date. However, such auto fascia is also problematic in that the original fascia is lost from the excised site, and that it easily adheres to the brain. Dry human dura mater is a dura mater supply material, which is produced by treating the dura mater collected from the dead body with radioactive rays. This material was the best among those that had ever been produced. However, the possibility emerged that prions reportedly responsible for Creutzfeldt-Jakob disease exist in the dura mater. It was then reported that a patient became affected with Creutzfeldt-Jakob disease through the dry human dura mater. In consequence, the use of dry human dura mater was completely prohibited in 1998.

At present, ePTFE (expanded polytetra-fluoroethylene) certified by the Ministry of Health, Labor and Welfare is the only material that can be used as a dura mater supply material other than the aforementioned auto fascia. Since ePTFE is a polymeric material, it has no adhesive properties to living bodies. This is advantageous in that the material does not adhere to the brain. On the other hand, since ePTFE has poor contractility, the spinal fluid leaks through pin holes. Thus, it is necessary to suture the operative site using a special surgical suture. Moreover, since ePTFE does not have adhesive properties to living bodies, spinal fluid leakage occurs even from gaps on a sutured surface. Furthermore, since ePTFE does not have adhesive properties also to peripheral tissues, there is a high possibility that it functions only as a simple skeletal material. A large number of attempts have been made to utilize such ePTFE to as great an extent. All of these attempts relate to a technique of using ePTFE as a skeletal material for the subsequent formation of fibrous tissues around the ePTFE.

As a method of treating the surface of an artificial material with ions, a method involving plasma treatment has been known (Japanese Patent Application No. 10-302170). This method comprises improving adhesive properties by modifying the surface of the material. A plasma-treated layer obtained by the plasma treatment method is unstable in living bodies, and it has a risk of decomposing or peeling off over time. In living bodies, it is necessary to maintain a stable cell adhesion layer over a long period of time. When the aforementioned plasma treatment method is particularly applied to the artificial dura mater, although the material adheres to the contact surface of the cranial bone at the initial stage, it has a risk of peeling off after a long period of time.

It has also been reported that the surface layer of an in vivo embedded material is modified using ions with higher energy than the ions used in the plasma treatment, so as to enhance antibacterial properties (Japanese Patent Application No. 5-148994). The main purpose of this method is to reduce the infectivity of the embedded material.

DISCLOSURE OF THE INVENTION

In order to fix medical materials used in vivo for surgical operations, such as an artificial blood vessel, an artificial dura mater, or a patch material for repairing the heart or blood vessels, to tissues for a therapeutic purpose, a method of fixing these materials to a living body via anastomosis has been adopted. When such a medical material is anastomosed with a living body using a surgical suture, however, the blood or spinal fluid can leak from holes on the material through which the needle has passed. Accordingly, in general, such leakage is prevented by inducing blood coagulation by applying pressure on an affected area, or by using a tissue adhesive known as fibrin glue.

It is an object of the present invention to provide a means for improving the affinity of an in vivo embedded material such as an artificial blood vessel or an artificial dura mater with a tissue adhesive, so as to quickly prevent the leakage of the blood or spinal fluid.

As a result of intensive studies directed towards achieving the aforementioned object, the present inventors have found that ePTFE that has been irradiated with an Ne ion beam has a higher affinity with a tissue adhesive than that of unirradiated ePTFE, thereby completing the present invention.

Thus, the present invention provides a polymeric material used in combination with a tissue adhesive, which comprises carbon or silicon as a constitutional element, and at least a portion of the surface of which is modified by ion bombardment.

The tissue adhesive is preferably fibrin glue.

The polymeric material comprising carbon or silicon as a constitutional element is preferably expanded polytetra-fluoroethylene (ePTFE), polylactic acid, or polyglactin.

The modification by ion bombardment is preferably carried out by irradiation with ions at a dose ($\phi$) of $1\times10^{12} \leq \phi \leq 1\times10^{16}$ ions/cm$^2$.

The polymeric material of the present invention is preferably used for an artificial dura mater, an artificial blood vessel, a patch used for the heart or blood vessel, or a surgical suture.

In another aspect, the present invention provides a method for producing a polymeric material used in combination with a tissue adhesive, which is characterized in that at least a portion of the surface of the polymeric material comprising carbon or silicon as a constitutional element is irradiated with ions at a dose ($\phi$) of $1\times10^{12} \leq \phi \leq 1\times10^{16}$ ions/cm$^2$.

In another aspect, the present invention provides a method for improving the affinity of a polymeric material comprising carbon or silicon as a constitutional element with a tissue adhesive, which is characterized in that at least a portion of the surface of the polymeric material is irradiated with ions at a dose ($\phi$) of $1\times10^{12} \leq \phi \leq 1\times10^{16}$ ions/cm$^2$.

BEST MODE FOR CARRYING OUT THE INVENTION

Figure 1:
FIG. 1 shows the interaction of unirradiated ePTFE with fibrin glue, which was observed 1 month after application of the unirradiated ePTFE to the rabbit. The unirradiated ePTFE did not adhere to fibrin glue.

The embodiments of the present invention will be described in detail below.

The polymeric material of the present invention is used in combination with a tissue adhesive. The polymeric material of the present invention comprises carbon or silicon as a constitutional element, and it is characterized in that at least a portion of the surface thereof is modified by ion bombardment.

In the present invention, a polymeric material comprising carbon or silicon as a constitutional element is irradiated with an ion beam, so as to improve the affinity of the material with a tissue adhesive, thereby preventing the leakage of the blood or spinal fluid. The present invention also relates to a method for treating the surface layer of a polymeric material, which comprises irradiating the above-described polymeric material with an ion beam, so as to improve the affinity of the material with a tissue adhesive.

When the blood vessel injured due to abdominal aortic aneurysm or the like is treated using an artificial blood vessel, the living blood vessel is connected with the artificial blood vessel by suturing with a surgical suture. However, in the case of using an artificial blood vessel made from a polyester or a fluorine compound, the blood leaks through pin holes, even using a surgical suture made from the same material.

Moreover, when a nidus is excised from the heart or blood vessel, the absent portion should be repaired. In a case of seaming a repair material with the blood vessel or heart also, the blood or tissue fluid leaks through pin holes. In the field of neurosurgery, when craniotomy is conducted to treat cerebral tumor, subarachnoid hemorrhage, a wound caused by traffic accident, and so on, the cranial dura mater is lost. An artificial dura mater is used to compensate for such loss of the cranial dura mater. However, as in the case of the artificial blood vessel, spinal fluid leaks through pin holes.

In many cases, a tissue adhesive known as fibrin glue is used to prevent such leakage of the blood vessel or spinal fluid. Among materials used for artificial blood vessel or dura mater, fluorine compound materials have extremely poor properties to adhere to fibrin glue, and thus, these materials are insufficient for preventing the leakage of the blood or spinal fluid.

In the present invention, the surface layers of these artificial materials are irradiated with an ion beam according to the ion implantation method, so as to improve the adhesive properties of the materials to fibrin glue. Such ion beam treatment can be carried out not only on an artificial dura mater, an artificial blood vessel, or a patch used for the heart or blood vessel, but also on the surface layer of a surgical suture used for connecting these artificial materials with living bodies. The adhesive properties of an artificial material to fibrin glue are improved by modifying the surface layer of a surgical suture with a beam.

A polymeric material used in the present invention, which comprises carbon or silicon as a constitutional element, is not particularly limited. Any material can be used, as long as it has biocompatibility and handlability. For example, fluorocarbon resin molded products such as expanded polytetrafluoroethylene (ePTFE) or suicides such as silicone can be used. Polymeric materials preferably used in the present invention may include expanded polytetra-fluoroethylene (ePTFE) and biodegradable polymers (e.g. polylactic acid, polyglactin, etc.). Of these, expanded polytetra-fluoroethylene (ePTFE) is particularly preferable.

At least a portion of the surface of the polymeric material of the present invention is modified by ion bombardment. Examples of ion species to be implanted may include $H^+$, $He^+$, $C^+$, $N^+$, $Ne^+$, $Na^+$, $N_2^+$, $O_2^+$, $Ar^+$, $Kr^+$, and $Xe^+$. However, examples are not limited thereto, unless such ion species is eluted and inhibits the affinity of the polymeric material with a tissue adhesive. Preferred examples may include $Ne^+$, $Ar^+$, $Kr^+$, and $Xe^+$.

The dose $\phi$ (amount of irradiation) is preferably in a range of $1\times10^{12} \leq \phi \leq 1\times10^{16}$ ions/cm$^2$. If the dose is lower than $10^{12}$ ions/cm$^2$, its effect of significantly improving the affinity of the polymeric material with a tissue adhesive decreases. If the dose is higher than $10^{16}$ ions/cm$^2$, the polymeric material is easily disrupted. Thus, both the cases are not preferable. The dose $\phi$ is more preferably in a range of $1\times10^{13} \leq \phi \leq 1\times10^{15}$ ions/cm$^2$.

With regard to ion acceleration energy, it is considered that energy transfer mechanism is varied depending on the level of such energy. Practically, the ion acceleration energy can be set within a range between several tens of keV and several MeV. It is more preferably set between 50 keV and 2 MeV.

Beam current density is preferably set in a range that does not exceed 0.5 $\mu$A/cm$^2$. This is because if such beam current density is too high, the temperature of the polymeric material as a target excessively increases, and the polymeric material itself thereby degenerates, and also because there is a risk that the affinity of the material with a tissue adhesive decreases.

A means for giving ion bombardment in the present invention may be ion implantation. Such ion implantation reaction is limited to an interaction between an ion beam and a material to which ions are implanted (target material). In addition, by selecting ion implantation energy, ions can be embedded at any given depth from the surface. Thus, ion implantation is extremely excellent in controllability. This is a characteristic that plasma treatment does not have. When ions are implanted, electron stopping capability acts on ions with a relatively low mass at the initial stage of diffusion, and nuclear stopping capability acts on ions with a relatively high mass from the initial stage. In spite of such a mechanical difference, the implanted ions heat the polymeric material due to lattice vibration (thermal nonequilibrium state), and cause dissolution, amorphization, and the like.

The polymeric material of the present invention is used in combination with a tissue adhesive. Preferred examples of a tissue adhesive may include fibrin glue and a cyanoacrylate instant adhesive that is a polymeric adhesive. Conventionally, suture has been carried out with a thread such as silk thread or catgut and a needle in surgical operations. For such suture, an adhesive has also been used. By the conventional suture methods, the suture of small blood vessels together or the repair of blood vessels have often been difficult. In addition, the conventional methods have also been problematic in that it generally takes a considerable period of time for suturing and in that ugly scar remains after suturing. A tissue adhesive is adopted as a means for solving such problems.

Fibrin glue is composed of fibrinogen freeze-dried powders, a fibrinogen-dissolving solution, thrombin freeze-dried powders, and a thrombin-dissolving solution. Fibrinogen freeze-dried powders are dissolved in a fibrinogen-dissolving solution, so as to obtain solution A. Thrombin freeze-dried powders are dissolved in a thrombin-dissolving solution, so as to obtain solution B. The thus dissolved solutions are laminated at equivalent volumes on an adhesive site. Otherwise, both the solutions are mixed with each other at equivalent volumes, and the mixture is applied thereto. Fibrin glue is a physiological tissue adhesive, which utilizes the final stage of blood coagulation. Fibrinogen contained in the fibrin glue becomes a soluble fibrin clot by the action of thrombin. Then, the fibrin clot becomes a urea-insoluble stable fibrin clot with physical strength by the action of the blood clotting factor XIII activated with thrombin in the presence of calcium ions. The thus obtained fibrin clot acts to adhere and close tissues. Fibroblasts grow in this stable fibrin clot, and collagen fibers or granulation matrix components are generated. Thus, the tissues are repaired, then reaching complete recovery. A specific example of such fibrin glue may be Bolheal (product name) (Chemo-Sero-Therapeutic Research Institute (Kaketsuken)).

Surgical treatments wherein fibrin glue is used for the purpose of fixing living tissues may include occlusion of bleeding injuries fixation of broken bones, anastomosis of peripheral nerves or small blood vessels, reinforcement of tendon adhesion or tendon suture, and adhesion of parenchymal organs. Moreover, when an artificial product such as an artificial dura mater or artificial blood vessel is anastomosed with living tissues, fibrin glue is used to prevent the spinal fluid or blood from leaking through pin holes. Likewise, fibrin glue is used together with a patch for repairing the absent portion of the heart or blood vessel, so as to prevent the blood from leaking through pin holes. In particular, ePTFE has been problematic in that it has poor adhesive properties with fibrin glue. However, such a problem has been solved by modifying at least a portion of the surface thereof by ion bombardment according to the present invention.

The present invention will be more specifically described in the following examples. However, the examples are not intended to limit the scope of the present invention.

EXAMPLES

(1) Ion Irradiation Treatment

A male Japanese white rabbit with a body weight of 2.5 to 3.0 kg was used in the experiment. The scalp of the rabbit was excised in a coronary form under general anesthesia with pentobarbital, so that the skull was exposed. Expanded polytetra-ethylene (ePTFE) irradiated with an ion beam ($Ne^+$, 150 keV, $5 \times 10^{14}$ ions/cm$^2$) using a 200 keV ion implanter (Riken, Japan) was used as a sample. The periosteum covering the surface of the skull was completely removed, and the cranial bone was then removed, so that the cranial dura mater was exposed. Thereafter, a hole with a diameter of several millimeters was made on a portion of the dura mater. The sample was placed on the dura mater, such that the non-irradiated face thereof was allowed to come into contact with the dura mater, and thus that the ion beam-irradiated face thereof was placed on the scalp side. Thereafter, a tissue adhesive (fibrin glue; Bolheal (product name); Chemo-Sero-Therapeutic Research Institute (Kaketsuken)) was dropped on the ion beam-irradiated face and then excess solution was removed. The remaining tissue adhesive was allowed to fix with the remaining cranial bone. As a control, a non-irradiated sample was also subjected to the same above operations. After dropping fibrin glue, the scalp was anastomosed with the skull, and the affected area was then covered.

(2) Observation

(a) Observation by Naked Eyes

Several minutes after dropping of fibrin glue, the ion beam-irradiated face favorably adhered to the peripheral bone tissues. In contrast, the adhesive force of the untreated expanded polytetra-fluoroethylene was weak to such an extent that it moved by adding a weak force with tweezers.

(b) Observation by Histological Tissue Examination

On the second week after the sample had been embedded, the rabbit was sacrificed with Nembutal. Thereafter, the affected area was removed together with the peripheral tissues thereof in the form of a mass, and it was immobilized with 10% buffer formalin. On the ion beam non-treated face, fibrin glue did not adhere to ePTFE at all. Thus, in order to avoid that the ePTFE was separated from the tissues, the sample was excised together with the peripheral tissues thereof. After the skull was decalcified, the sample placed on the dura mater was embedded in paraffin. The sample was subjected to hematoxylin-eosin staining and Masson trichrome staining, and then observed with a microscope.

Figure 2:
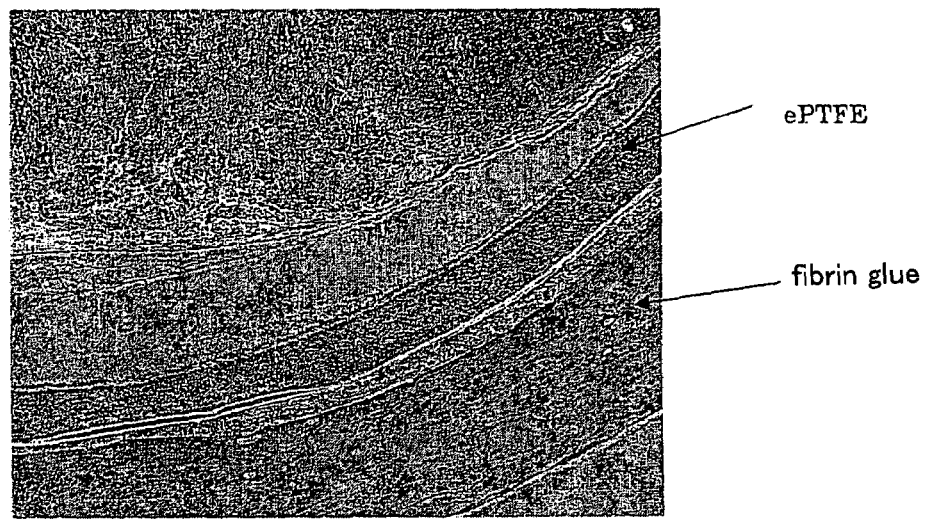
FIG. 2 shows the interaction of ion beam-irradiated ePTFE with fibrin glue, which was observed 1 month after application of the ion beam-irradiated ePTFE to the rabbit. The ion beam-irradiated ePTFE adhered to fibrin glue via cells.

As a result, no adhesion was observed between the untreated ePTFE and fibrin glue on the second week (FIG. 1). On the other hand, the ion beam-treated ePTFE adhered extremely favorably to fibrin glue (FIG. 2).

(3) Brain Pressure Addition Experiment

Figure 3:
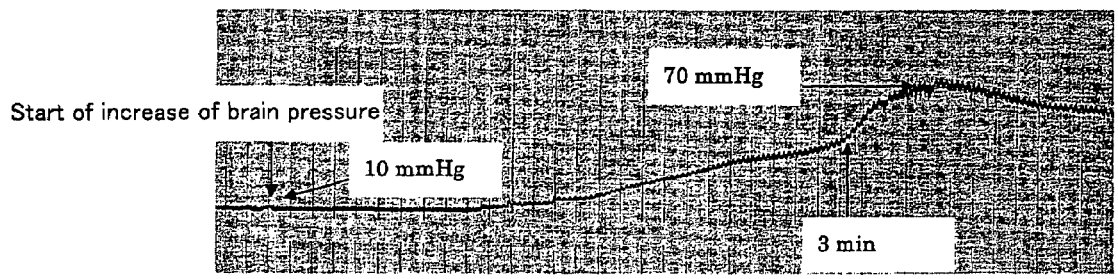
FIG. 3 shows a curve relating to an increased pressure in the brain of the rabbit, to which the ion-beam irradiated dura mater was applied.

The scalp of a rabbit, to which the ion beam-irradiated sample was embedded for 4 weeks under the same above conditions, was removed under anesthesia, and the portion in which the sample was embedded was exposed. Thereafter, a hole with a diameter of approximately 1 mm was made on a cranial bone portion different from the above sample embedded portion. A catheter for applying pressure to the brain was inserted into one hole. Another catheter for measuring the brain pressure was inserted into the other hole. The catheter was connected with a syringe pump, and the brain pressure was increased. Thereafter, an artificial dura mater and fibrin glue immobilizing the artificial dura mater were observed, and it was confirmed whether or not these materials were peeled off due to the increased brain pressure. For pressurization, a 50-ml syringe was connected with a syringe pump, and a pressure was then applied at a rate of 1 ml/min. FIG. 3 shows the relationship between time and brain pressure. The brain pressure was approximately 10 mmHg before applying the pressure. 1.5 minutes after applying the pressure, the brain pressure began to increase. The brain pressure increased slowly at the initial stage, but it increased drastically from 3 minutes after the application of the pressure. The brain pressure reached 70 mmHg. However, during such pressurization, the leakage of spinal fluid was not observed from the ion beam-irradiated artificial dura mater that was immobilized with fibrin glue, and thus, it showed good sealing performance.

(4) In Vitro Adhesive Force Evaluation Test

The adhesion of the ion beam-irradiated ePTFE with fibrin glue was evaluated in vitro, using a pressure device.

Figure 4:
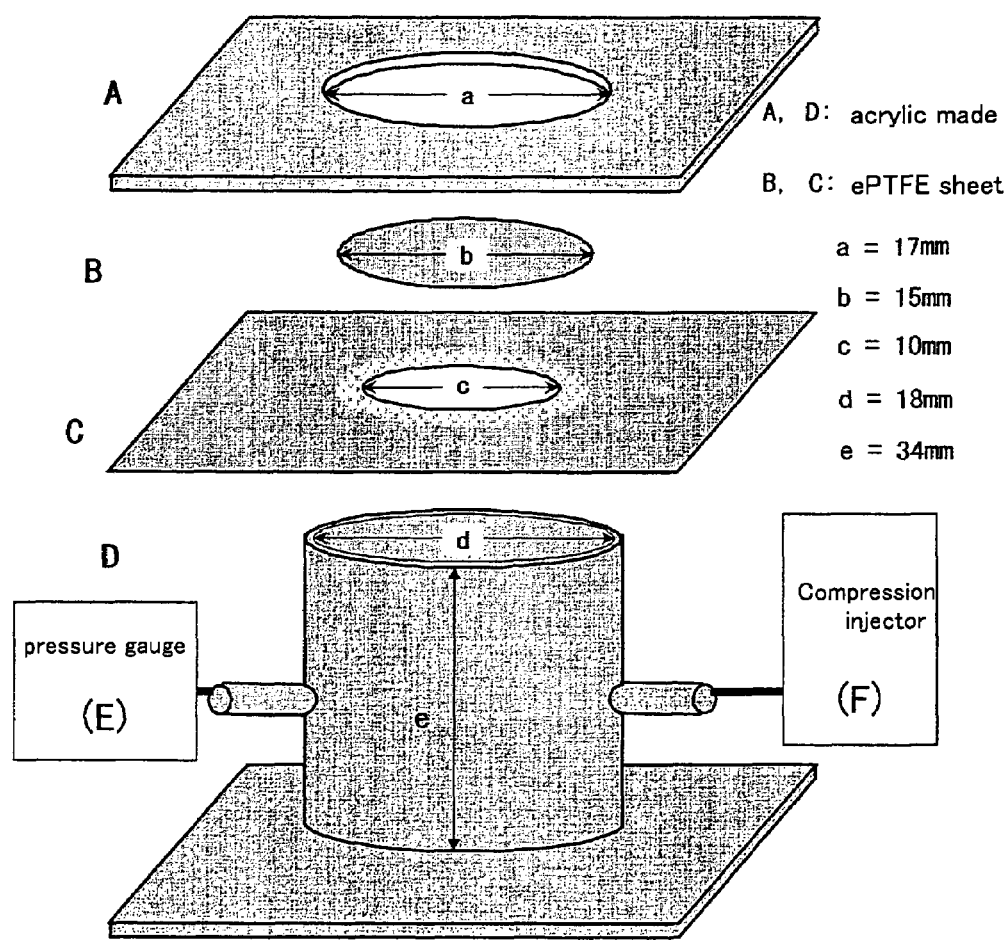
FIG. 4 shows a device used for a pressure endurance test.

In order to evaluate the adhesion, two ion beam-irradiated faces with the same conditions were allowed to adhere to each other using fibrin glue, and the adhesive force was measured. With regard to ion beam irradiation to ePTFE, $He^+$, $Ne^+$, $Ar^+$, and $Kr^+$ ions were irradiated at an acceleration energy of 150 keV at a dose of $1\times10^{14}$, $5\times10^{14}$, and $1\times10^{15}$ ions/cm$^2$. FIG. 4 shows a pressure resistance device.

In order to evaluate the adhesiveness of fibrin glue to unirradiated ePTFEs and ion beam-irradiated ePTFEs, a sample that was cut into a round form with a diameter of 15 mm was connected with a square sample having a round hole with a diameter of 10 mm such that both non ion irradiated faces or both ion beam irradiated faces were adhere to each other using fibrin glue. A fibrinogen solution was applied around pore C, a thrombin solution was added dropwise thereto, and B was placed on it. While mixing the two solutions, B was allowed to closely come into contact with C. The contacted portion corresponds to the overlapped portion between the circle with a diameter of 15 mm and the circle with a diameter of 10 mm, which was fixed with fibrin glue.

ePTFE (B+C) fixed with fibrin glue was immobilized on the upper portion of an acryl cylinder (D). 30 minutes later, the fixed portion B+C was placed on the cylinder D, which was filled with water stained with ink. An acryl plate A having a hole with an inner diameter of 17 mm was further placed thereon, and the pressure was applied thereto, so that the device was immobilized.

Under these conditions, water was injected from a pressure-applying port F into the cylinder D at a rate of 60 ml/h. During this operation, the pressure in the cylinder D was measured using a pressure sensor via a monitoring port E, until water leaked from the contacted portion of B and C.

Figure 5:
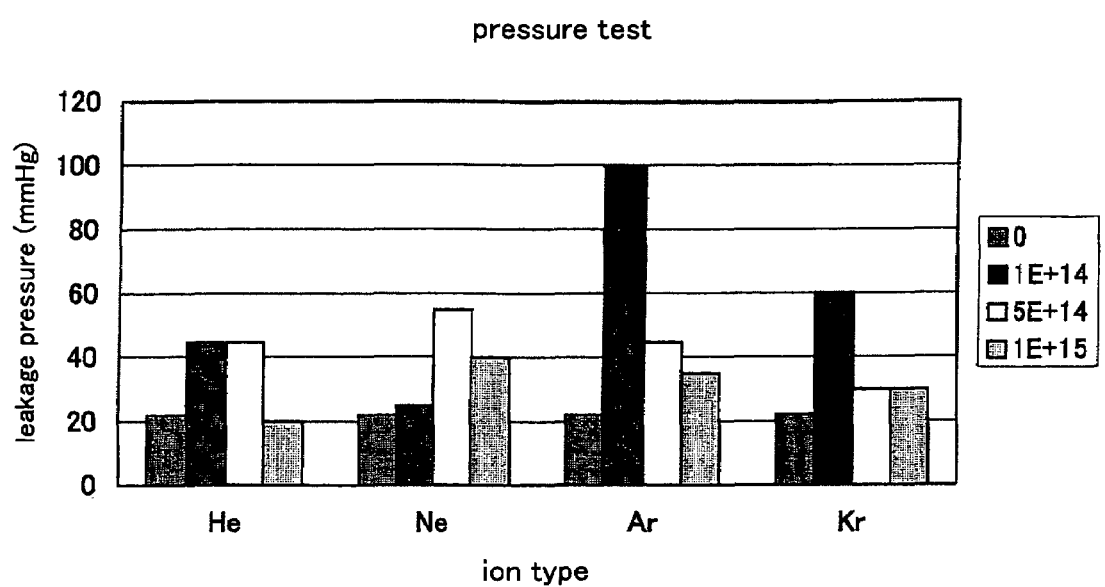
FIG. 5 shows the relationship among a leakage critical pressure, ion species, and a dose of radiation in a pressure test. 0 (zero) in legends represents an unirradiated sample.

FIG. 5 shows the relationship among a leakage critical pressure, ion species, and a dose of radiation in a pressure test. Water leaked from the contacted portion of two unirradiated ePTFE faces by applying a pressure of approximately 20 mmHg. In contrast, in the case of the adhesion of two ion beam-irradiated ePTFE faces, the withstanding pressure significantly increased. In particular, the critical pressure increased to 100 mmHg, when a sample irradiated with an $Ar^+$ ion beam at a dose of $1\times10^{14}$ ions/cm$^2$ was used. Thus, it showed favorable adhesive properties.

INDUSTRIAL APPLICABILITY

The present invention enables the improvement of the affinity of a material that is embedded in a living body, such as an artificial blood vessel or an artificial dura mater, with a tissue adhesive. When the polymeric material of the present invention is used as a material embedded in a living body, such as an artificial blood vessel or an artificial dura mater, it can prevent the leakage of the blood or spinal fluid.

The invention claimed is:

1. A method for improving affinity with a fibrin glue of a polymeric material comprising carbon or silicon as a constitutional element, the polymeric material comprising expanded polytetra-fluoroethylene or silicone, comprising irradiating at least a portion of a surface of the expanded polytetra-fluoroethylene or silicone with ions at a dose ($\phi$) of $1\times10^{12} \leq \phi \leq 1\times10^{16}$ ions/cm$^2$ to form an ion-modified expanded polytetra-fluoroethylene or silicone; and applying the fibrin glue to the irradiated at least a portion of a surface of the expanded polytetra-fluoroethylene or silicone, wherein the ion is $He^+$, $Ne^+$, $Ar^+$, or $Kr^+$.

2. The method according to claim 1 wherein the ion-modified expanded polytetra-fluoroethylene or silicone includes a non-irradiated portion and the non-irradiated surface is placed into contact with dura mater.

3. The method according to claim 1 wherein the expanded polytetra-fluoroethylene or silicone is an artificial dura mater, an artificial blood vessel, a patch for the heart or blood vessel, or a surgical suture.

4. The method according to claim 1 wherein the expanded polytetra-fluoroethylene or silicone comprises expanded polytetra-fluoroethylene.

5. The method according to claim 1 wherein the expanded polytetra-fluoroethylene or silicone is an artificial dura mater.

6. The method according to claim 1 wherein the irradiating at least a portion of a surface of the expanded polytetra-fluoroethylene or silicone comprises irradiating with ions at a dose ($\phi$) of $1\times10^{13} \leq \phi \leq 1\times10^{15}$ ions/cm$^2$.

7. The method according to claim 1 wherein the expanded polytetra-fluoroethylene or silicone comprises silicone.

8. The method according to claim 2 wherein the expanded polytetra-fluoroethylene or silicone comprises expanded polytetra-fluoroethylene.

9. The method according to claim 2 wherein the expanded polytetra-fluoroethylene or silicone comprises silicone.

10. The method according to claim 3 wherein the expanded polytetra-fluoroethylene or silicone comprises expanded polytetra-fluoroethylene.

11. The method according to claim 3 wherein the expanded polytetra-fluoroethylene or silicone comprises silicone.

12. The method according to claim 5 wherein the expanded polytetra-fluoroethylene or silicone comprises expanded polytetra-fluoroethylene.

13. The method according to claim 5 wherein the expanded polytetra-fluoroethylene or silicone comprises silicone.

14. The method according to claim 6 wherein the expanded polytetra-fluoroethylene or silicone comprises expanded polytetra-fluoroethylene.

15. The method according to claim 6 wherein the expanded polytetra-fluoroethylene or silicone comprises silicone.

* * * * *